(12) United States Patent
Keusenkothen et al.

(10) Patent No.: US 10,273,196 B2
(45) Date of Patent: *Apr. 30, 2019

(54) HYDROCARBON DEHYDROCYCLIZATION

(71) Applicant: ExxonMobil Chemical Patents Inc., Baytown, TX (US)

(72) Inventors: Paul F. Keusenkothen, Houston, TX (US); John S. Buchanan, Flemington, NJ (US); John S. Coleman, Houston, TX (US); Seth M. Washburn, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 113 days.

This patent is subject to a terminal disclaimer.

(21) Appl. No.: 15/240,531

(22) Filed: Aug. 18, 2016

(65) Prior Publication Data

US 2017/0088491 A1 Mar. 30, 2017

Related U.S. Application Data

(60) Provisional application No. 62/313,306, filed on Mar. 25, 2016, provisional application No. 62/232,609, filed on Sep. 25, 2015.

(30) Foreign Application Priority Data

Jun. 10, 2016 (EP) ..................... 16173980

(51) Int. Cl.
*C07C 2/76* (2006.01)
*B01J 8/02* (2006.01)
*C10G 11/00* (2006.01)

(52) U.S. Cl.
CPC .............. *C07C 2/76* (2013.01); *B01J 8/0278* (2013.01); *B01J 8/0285* (2013.01); *C10G 11/00* (2013.01); *B01J 2208/00548* (2013.01); *B01J 2208/02* (2013.01); *C07C 2529/40* (2013.01); *C07C 2529/65* (2013.01); *C07C 2529/70* (2013.01); *C07C 2529/80* (2013.01)

(58) Field of Classification Search
CPC .......................................... B01J 38/12–38/38
See application file for complete search history.

(56) References Cited

U.S. PATENT DOCUMENTS

| | | |
|---|---|---|
| 3,960,978 A | 6/1976 | Givens et al. |
| 4,016,218 A | 4/1977 | Haag et al. |
| 4,021,502 A | 5/1977 | Plank et al. |
| 4,150,062 A | 4/1979 | Garwood et al. |
| 4,227,992 A | 10/1980 | Garwood et al. |
| 4,456,781 A | 6/1984 | Marsh et al. |
| 4,704,497 A | 11/1987 | Gottlieb et al. |
| 4,855,522 A | 8/1989 | Diaz |

(Continued)

FOREIGN PATENT DOCUMENTS

WO 2010140005 12/2010

*Primary Examiner* — Philip Y Louie
*Assistant Examiner* — Alyssa L Cepluch (57) ABSTRACT

The invention relates to hydrocarbon dehydrocyclization to produce products such as aromatic hydrocarbon, to equipment and materials useful for dehydrocyclization, to processes for carrying out dehydrocyclization, and to the use of dehydrocyclization for, e.g., natural gas upgrading. The dehydrocyclization is carried out in a catalytic reaction zone of a reverse-flow reactor.

18 Claims, 2 Drawing Sheets

(56) References Cited

U.S. PATENT DOCUMENTS

| | | |
|---|---|---|
| 5,026,937 A | 6/1991 | Bricker |
| 5,510,557 A * | 4/1996 | Gartside ................. C07B 35/04 208/34 |
| 5,563,314 A * | 10/1996 | Agaskar ................ C07C 5/3335 585/315 |
| 5,633,417 A | 5/1997 | Beck et al. |
| 5,675,047 A | 10/1997 | Beck et al. |
| 6,670,517 B1 | 12/2003 | Abichandani et al. |
| 7,491,250 B2 | 2/2009 | Hershkowitz et al. |
| 7,759,535 B2 * | 7/2010 | Iaccino .................... C07C 2/76 518/702 |
| 7,815,873 B2 | 10/2010 | Sankaranarayanan et al. |
| 7,846,401 B2 | 12/2010 | Hershkowitz et al. |
| 7,943,808 B2 | 5/2011 | Hershkowitz et al. |
| 8,692,043 B2 | 4/2014 | Lauritzen et al. |
| 8,754,276 B2 | 6/2014 | Buchanan et al. |
| 8,835,706 B2 | 9/2014 | Iyer et al. |
| 9,144,790 B2 | 9/2015 | Lauritzen et al. |
| 9,394,214 B2 * | 7/2016 | Henao ....................... C07C 2/84 |
| 2007/0249880 A1 | 10/2007 | Iaccino et al. |
| 2009/0209794 A1 | 8/2009 | Lauritzen et al. |
| 2012/0003214 A1 | 1/2012 | Nuttall et al. |
| 2014/0323783 A1 | 10/2014 | Keusenkothen et al. |
| 2015/0065769 A1 | 3/2015 | Henao et al. |

* cited by examiner

HYDROCARBON DEHYDROCYCLIZATION

CROSS-REFERENCE TO RELATED APPLICATIONS

This invention claims priority to and the benefit of U.S. Patent Application Ser. Nos. 62/232,609 filed Sep. 25, 2015; 62/313,306, filed Mar. 25, 2016; and European Patent Application Nos. 15195311.4 filed Nov. 19, 2015 and 16173980.0 filed Jun. 10, 2016, all of which are incorporated by reference in their entireties. The following related cases are also incorporated by reference in their entireties: U.S. Patent Application Ser. No. 62/234,262; European Patent Application No. 15195314.8; U.S. Patent Application Ser. No. 62/234,240; European Patent Application No. 15197698.2; U.S. Patent Application Ser. No. 62/247,795; European Patent Application No. 15197700.6; U.S. Patent Application Ser. No. 62/248,374; European Patent Application No. 15197702.2; U.S. Patent Application Ser. No. 62/253,268; U.S. Patent Application Ser. No. 62/298,655; European Patent Application No. 16167672.1; U.S. Patent Application Ser. No. 62/326,918; European Patent Application No. 16175163.1; U.S. Patent Application Ser. No. 62/299,730; European Patent Application No. 16167395.9; U.S. Patent Application Ser. No. 62/313,288 and European Patent Application No. 16173587.3.

FIELD

The invention relates to hydrocarbon dehydrocyclization to produce products such as aromatic hydrocarbon, to equipment and materials useful for dehydrocyclization, to processes for carrying out dehydrocyclization, and to the use of dehydrocyclization for, e.g., natural gas upgrading.

BACKGROUND

Aromatic hydrocarbon compounds such as benzene are frequently used for producing transportation fuels and petrochemicals such as styrene, phenol, nylon, polyurethanes and many others. Benzene can be produced, e.g., by steam cracking and naphtha reforming. During steam cracking, a $C_{2+}$ hydrocarbon feed reacts in the presence of steam under high-temperature pyrolysis conditions to produce a product comprising molecular hydrogen, $C_{4-}$ olefin, other $C_{4-}$ hydrocarbon, and $C_{5+}$ hydrocarbon including aromatic hydrocarbon. The yield of aromatic hydrocarbon from steam cracking is generally much less than the yield of light hydrocarbon, and processes of significant complexity are typically needed for aromatics separation and recovery. Naphtha reforming catalytically produces a product having a much greater content of aromatic hydrocarbon than does steam cracker effluent, but the naphtha feed is itself useful for other purposes such as motor gasoline blendstock.

Attempts have been made to overcome these difficulties, and provide an efficient process for producing aromatic hydrocarbon at high yield from a relatively inexpensive feed. For example, processes have been developed for producing light aromatic hydrocarbon (e.g., benzene, toluene, and xylenes—"BTX") from paraffinic $C_1$-$C_4$ feeds. The processes typically utilize a catalyst having a molecular sieve component e.g., ZSM-5, and a dehydrogenation component, such as one or more of Pt, Ga, Zn, and Mo. These conventional processes typically operate at high temperature and low pressure. Although these conditions increase the yield of aromatic hydrocarbon, they also lead to an increased rate of catalyst deactivation, mainly resulting from increased catalyst coking.

Reverse-flow reactors can be used to lessen the amount of catalyst coking. The reactor carries out a catalytic reaction such as hydrocarbon aromatization during forward flow, which deposits coke proximate to the catalyst. Following the forward flow reaction, a reverse-flow oxidation reaction combusts at least a portion of the accumulated coke. For example, U.S. Pat. No. 4,704,497 discloses carrying out catalytic dehydrogenation of a hydrocarbon feed in forward-flow, and then removing coke deposits on the dehydrogenation catalysts by conveying an oxygen-containing gas through the reactor in reverse-flow. Since at least a portion of any accumulated coke is removed from the catalyst by oxidation during reverse-flow, the long-term rate of catalyst coke accumulation can be controlled.

A more recent process, described in U.S. Pat. No. 8,754,276, includes carrying out a catalytic dehydrogenation reaction in a reaction zone of a reverse-flow reactor. The catalytic dehydrogenation is operated in forward flow to produce unsaturated products such as olefin and aromatic hydrocarbon (reaction mode). The reaction zone has a lesser temperature at the upstream end of the reaction zone. The temperature profile increases monotonically across the reaction zone to a greater temperature at the downstream end, with upstream and downstream being with respect to the flow of hydrocarbon feed. This temperature profile is said to benefit the catalytic dehydrogenation reaction by lessening undesired reversion reactions which produce products of greater saturation. Since the dehydrogenation reaction is endothermic, the reaction zone cools during dehydrogenation mode, which eventually lessens dehydrogenation efficiency. The reaction zone is reheated by operating the reactor in regeneration mode. During regeneration mode, a combustion mixture comprising oxidant and fuel is conveyed to the reactor. The fuel is combusted with the oxidant in a combustion zone located within the reactor. The combustion zone contains a selective combustion catalyst, and is located upstream of the reaction zone with respect to the flow of the combustion mixture. Heat transferred from the hot combustion products to the reaction zone reheats the reaction zone to a temperature sufficient for carrying out dehydrogenation mode operation. After the reactor is sufficiently reheated, regeneration mode is halted, and reaction mode operation is re-commenced. According to the patent, placing the selective combustion catalyst in the combustion zone ensures that combustion of the combustion mixture is carried out in the combustion zone, not in the reaction zone. Carrying out combustion within the reaction zone is said to be undesirable because it results in a deviation from the desired monotonic temperature profile, which during reaction mode would increase the undesirable reversion of product olefin and aromatic hydrocarbon to more saturated molecules. However, decreasing the amount of oxidant proximate to the dehydrogenation catalyst during the combustion mode also lessens the amount of catalyst coke that can be removed from the dehydrogenation catalyst.

Another way to control catalyst coking involves carrying out the aromatization processes with a decreased selectivity for catalyst coke. For example, U.S. Pat. No. 4,855,522 discloses using a dehydrocyclization catalyst comprising (a) an aluminosilicate having a silica:alumina molar ratio of at least 5 and (b) a compound of (i) Ga and (ii) at least one rare earth metal. The aromatization is carried out at a temperature ≥450° C. (e.g., 475° C. to 650° C.) and a pressure of from 1 bar to 20 bar. Other processes limit selectivity for catalyst coke by carrying out the reaction for a relatively short time (e.g., less than a day), and then halting the reaction so that the catalyst can be regenerated. For example, U.S. Patent Application Publication No. 2009/0209794 A1, and U.S. Pat. Nos. 8,692,043 and 9,144,790, disclose processes for aromatizing lower alkanes using a particulate catalyst, where the average catalyst particle residence time in the reaction zone between regeneration treatments is in the range of about 0.1 second to about 30 minutes. Maximum ethane conversion is about 63%, but the catalyst and process conditions which achieve appreciable ethane conversion also exhibit appreciable selectivity for methane.

It is desired to produce aromatic hydrocarbon from $C_{2+}$ non-aromatic hydrocarbon at greater feed conversion, particularly with less methane yield. Processes which operate at a space velocity (GHSV) greater than 1000 $hr^{-1}$, are particularly desired. Reverse-flow reactors suitable for carrying out such reactions are also desired.

SUMMARY OF THE INVENTION

Catalytic processes for dehydrocyclizing substantially non-aromatic $C_{2+}$ hydrocarbon in a reverse-flow reactor have been developed which feature greater feed conversion and typically less methane selectivity than conventional dehydrocyclization processes. Unexpectedly in view of the prior art, it has been found that catalytic dehydrocyclization processes carried out in a reverse-flow reactor are (i) less sensitive to deviations from a monotonically increasing temperature profile in the reaction zone and (ii) more sensitive to dehydrocyclization catalyst coking. In order to mitigate the decrease in feed conversion resulting from excessive coke accumulation, less than all of oxidant conveyed to the reactor during regeneration mode is consumed by combustion with a fuel upstream (with respect to oxidant flow) of the dehydrocyclization catalyst. A second portion of the oxidant (a portion which is not consumed by the fuel combustion), together with hot combustion products and optionally un-combusted fuel, is conveyed to the reaction zone for additional combustion which (i) removes catalyst coke deposits and (ii) provides additional heating in the reaction zone.

Accordingly, certain aspects of the invention relate to a process for dehydrocyclization of substantially non-aromatic hydrocarbon. The dehydrocyclization is carried out in a reverse-flow reactor which comprises a pre-heated reaction zone. A dehydrocyclization catalyst is located in the reaction zone. The dehydrocyclization catalyst comprises a molecular sieve component and a dehydrogenation component. During a first time interval, a forward flow of a feed comprising $C_{2+}$ non-aromatic hydrocarbon is conducted to the reaction zone. Heat is transferred from the pre-heated reaction zone to the feed to produce a forward flow of a heated feed and a cooled reaction zone. At least a portion of the heated feed flow's $C_{2+}$ non-aromatic hydrocarbon is reacted in the presence of the dehydrocyclization catalyst under dehydrocyclization conditions which include a temperature $\geq 400°$ C. and a pressure $\geq 0$ psi gauge (psig) (101 kPa). The reaction produces a forward flow of a reaction product comprising molecular hydrogen and aromatic hydrocarbon. The reaction also deposits coke on or proximate to the dehydrocyclization catalyst. The forward flow of reaction product is conducted out of the reaction zone and away from the reverse-flow reactor. At the end of the first time interval, the feed flow to the reaction zone is decreased or halted. Regeneration mode is carried out during a second time interval, during which a reverse flow of the fuel and a reverse flow of the oxidant are established. A first portion of the oxidant flow is combusted under combustion conditions with at least a portion of the fuel flow to produce a reverse flow of a first combustion product toward the reaction zone. A second portion of the oxidant flow is combusted within the reaction zone with at least a portion of the deposited coke to produce a reverse flow of a second combustion product in the reaction zone. Heat is transferred from the combustion products to the reaction zone to re-heat the reaction zone. The reverse flows of the first and second combustion products are conducted away from the reaction zone and out of the reverse-flow reactor. At the end of the second time interval, the reverse flows of fuel and oxidant are decreased or halted.

It has also been discovered that increased feed conversion can be achieved, even with relatively refractory feeds such as ethane, when the dehydrocyclization reaction is carried out in a reverse-flow reactor for a time duration of less than about 90 seconds. The increased conversion is achieved with appreciable selectivity for aromatic hydrocarbon (particularly BTX), but without a significant increase in the process's selectivity for catalyst coke.

DETAILED DESCRIPTION

Definitions

For the purpose of this description and dependent claims, the following terms are defined. The term "$C_n$" hydrocarbon means hydrocarbon having n carbon atom(s) permolecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, unsaturated hydrocarbon, and (iii) mixtures of hydrocarbons, and including mixtures of hydrocarbon compounds (saturated and/or unsaturated), such as mixtures of hydrocarbon compounds having different values of n.

The terms "alkane" and "paraffinic hydrocarbon" mean substantially-saturated compounds containing hydrogen and carbon only, e.g., those containing $\leq 1\%$ (molar basis) of unsaturated carbon atoms. As an example, the term alkane encompasses $C_2$ to $C_{20}$ linear, iso, and cyclo-alkanes. Aliphatic hydrocarbon means hydrocarbon that is substantially free of hydrocarbon compounds having carbon atoms arranged in one or more rings.

The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and "aromatic hydrocarbon" mean hydrocarbon compounds containing at least one aromatic ring. Non-aromatic hydrocarbon is hydrocarbon comprising ≤1 wt. % of carbon atoms included in aromatic rings.

The term "Periodic Table" means the Periodic Chart of the Elements, as it appears on the inside cover of The Merck Index, Twelfth Edition, Merck & Co., Inc., 1996.

The term "reaction zone" mean a location within a reactor, e.g., a specific volume within a reactor, for carrying out a specified reaction. A reactor or reaction stage can encompass one or more reaction zones. More than one reaction can be carried out in a reactor, stage, or zone. For example, a reaction stage can include a first zone for carrying out first and second reactions and a second zone for carrying out a third reaction, where the first reaction (e.g., dehydrocyclization) can be the same as or different from the second reaction, and the third reaction (e.g., $CO_2$ methanation) can be the same as the second reaction or different.

"Dehydrocyclization" means removing hydrogen from and cyclizing a non-cyclic hydrocarbon to produce aromatic hydrocarbon and typically (i) cyclo-paraffin and/or (ii) cyclo-olefin. Dehydrocyclization can be carried out in one step which includes both dehydrogenation and cyclization. Dehydrocyclization can be carried out in one step, in two steps, e.g., dehydrogenation followed by cyclization of the dehydrogenated intermediate; or in three or more steps, e.g., normal paraffin dehydrogenation, cyclization of the olefinic intermediate, and additional dehydrogenation (aromatization) of the cyclo-olefin intermediate. The dehydrocyclization (including any dehydrogenation carried out in connection with dehydrocyclization) is "non-oxidative" meaning that the reaction is carried out with little if any oxidative coupling of feed hydrocarbon, intermediate hydrocarbon (if any), or dehydrocyclization product.

The term "selectivity" refers to the production (weight basis) of a specified compound in a catalytic reaction. As an example, the phrase "a light hydrocarbon conversion reaction has 100% selectivity for aromatic hydrocarbon" means that 100% of the light hydrocarbon (weight basis) that is converted in the reaction is converted to aromatic hydrocarbon. When used in connection with a specified reactant, the term "conversion" means the amount of the reactant (weight basis) consumed in the reaction. For example, when the specified reactant is $C_4$ paraffinic hydrocarbon, 100% conversion means 100% of the $C_4$ paraffinic hydrocarbon is consumed in the reaction. Yield (weight basis) is conversion times selectivity.

Representative Reverse-Flow Reactors

The catalytic dehydrocyclization of substantially non-aromatic $C_{2+}$ hydrocarbon is carried out in a reverse-flow reactor. The reactor includes a reaction zone, and may optionally include additional zones, e.g., for combustion and/or heat transfer. The reaction zone includes at least one dehydrocyclization catalyst having molecular sieve and dehydrogenation components. The reverse-flow reactor operates in at least two modes: reaction mode and regeneration mode. During reaction mode, a forward-flow of a feed containing the $C_{2+}$ non-aromatic hydrocarbon is established in proximity to the dehydrocyclization catalyst. A forward flow of the reaction product is conducted away from the reaction zone and out of the reverse-flow reactor. The dehydrocyclization reaction is net-endothermic, resulting in reaction zone cooling. When the cooling and the accumulation of catalyst coke deposits curtail the desired conversion of non-aromatic hydrocarbon in the feed, the forward-flow of feed to the reactor and forward flow of reaction product away from the reactor is typically decreased or halted. Reactor regeneration is then carried out during a following regeneration mode.

During regeneration mode, reverse flows of oxidant and a gaseous fuel are established to the reverse-flow reactor. Reverse flow refers to a flow direction that is substantially the reverse of (opposite to) the direction of average feed flow. A substantially anti-parallel relationship between forward and reverse flow is preferable, e.g., where the average flow vector for the gaseous fuel (and/or oxidant) and the average flow vector for the $C_{2+}$ hydrocarbon feed lie along parallel lines but point in opposite directions, but is not required. Regeneration mode includes combusting the fuel with a portion of the oxidant to produce a hot combustion product. Heat is transferred from the hot combustion product to the reaction zone to reheat the reaction zone. Regeneration mode also includes removing at least a portion of the accumulated coke deposits. To do this, regeneration mode conditions are selected so that fuel combustion consumes less than all of the available oxidant. Typically, regeneration mode conditions are selected so that at least 0.1 wt. % of the available oxidant is not consumed by combustion with the fuel. Coke deposits are removed by oxidation (combustion) using at least a portion of the available oxidant that is not consumed by fuel combustion. The regenerated reactor can then be switched to reaction mode for continuing production of aromatic hydrocarbon.

The reverse flow reactor can be configured for alternating reaction mode and regeneration mode operation, e.g., by repeating reaction modes and regeneration modes. When insufficient conversion of the $C_{2+}$ hydrocarbon is achieved, a second reverse-flow reactor can be used downstream of the first reactor. All or a portion of the first reactor's reaction product, which typically includes unreacted $C_{2+}$ hydrocarbon feed, can be conducted to the second reactor (also in reaction mode operation) in forward flow for additional conversion. Although the first and second reactors can remain in series during regeneration mode, it is preferable for them to be operated in parallel. During parallel regeneration mode operation a first reverse flow of gaseous fuel and a first reverse flow of oxidant are conducted to the first reactor, and a second reverse flow of gaseous fuel and a second reverse flow of oxidant are conducted to the second reactor. Combustion products produced in the first and second reactor during regeneration mode can be combined and conducted away. The invention is compatible with the use of additional reactors, which may be operated in series and/or parallel with the first and second reactor.

Typically, reaction mode and regeneration mode operation in a reverse-flow reactor are repeated in sequence, for semi-continuous or continuous operation. Intervening steps between successive reaction and regeneration modes, e.g., one or more steps for admitting a forward or reverse flow of sweep gas to the reverse-flow reactor, can be carried out between reaction mode operation and regeneration mode operation, and vice versa. This can be beneficial, e.g., when it is desired to sweep water from the vicinity of the dehydrocyclization catalyst. Typically, water is produced during regeneration mode by oxidation of hydrogen released during coke combustion. When present in an excessive amount, the water can react with the dehydrocyclization catalyst, leading to undesirable catalyst de-alumination. Excess water can be removed from the reactor by flowing a substantially inert sweep gas though the reactor (in either forward or reverse flow) before re-commencing reaction mode. Continuous or semi-continuous operation can be characterized by a "cycle time", which constitutes the time duration from the start of a reaction step to the start of the next reaction step in the sequence, and includes the time duration of regeneration step(s) and any intervening steps (when used). Cycle time can be substantially constant over a plurality of repeated cycles, but this is not required.

Figure 1A:
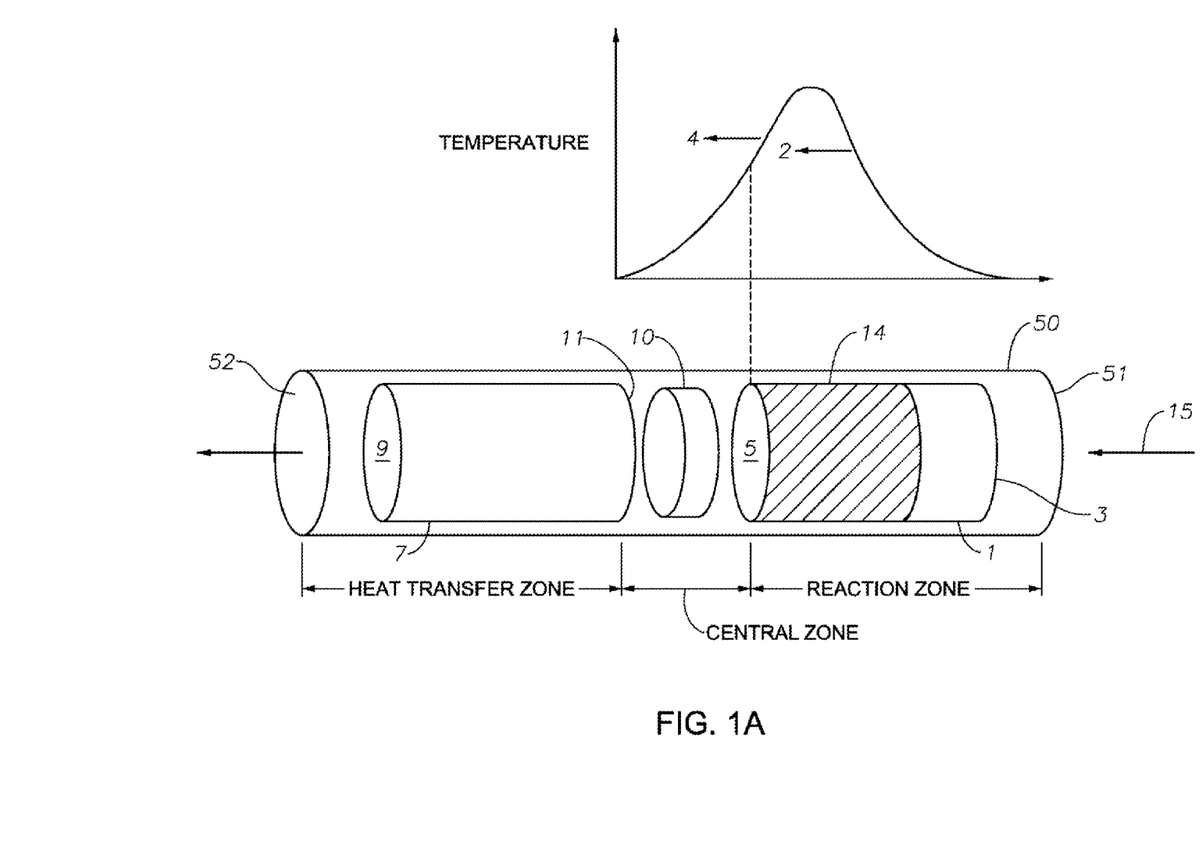
FIGS. 1A and 1B schematically show one form of a catalytic reverse flow reactor at the start of reaction mode (1A) and at the start of regeneration mode (1B).
Figure 1B:
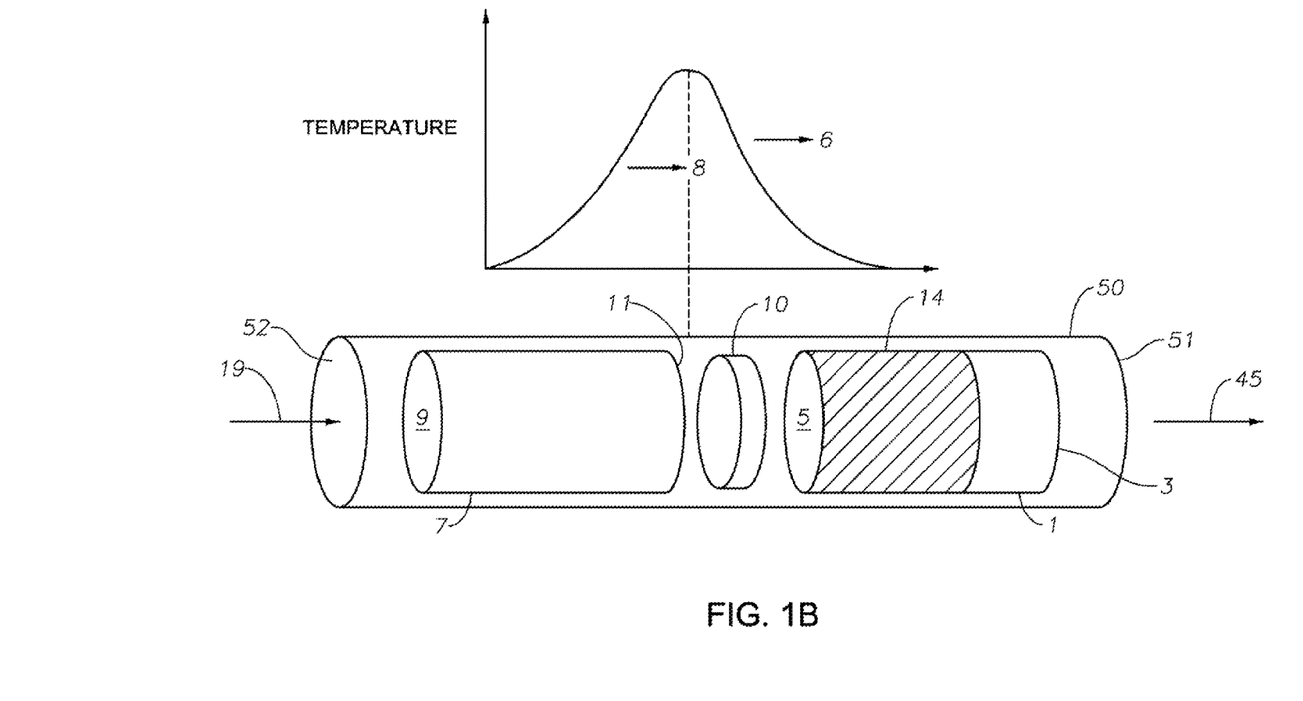

Certain aspects of the invention that are illustrated in FIGS. 1A and 1B will now be described in more detail. The invention is not limited to these aspects, and this description is not meant to foreclose other aspects within the broader scope of the invention.

Reverse-flow reactor 50 can have the form of an elongated tubular vessel having an internal volume which includes at least a reaction zone. Typically, the internal volume includes three zones: a reaction zone, a heat-transfer zone opposed to the reaction zone, and a third zone (typically a central zone) located between the heat-transfer and reaction zones. The zones are in fluidic communication with one another. The reactor vessel typically the form of an elongated tubular member of circular, elliptical, and/or polygonal cross section. Reactor 50 has at least two apertures open to the internal volume, which can have the form of opposed apertures 51 and 52. Typically one of the apertures is located at each reactor termination as shown.

The reaction zone typically includes at least one thermal mass (thermal mass 1) for transferring heat to/from reactants used and products made during the reaction and regeneration modes. For example, the thermal mass can comprise bedding or packing material that is effective in storing and transferring heat, such as glass or ceramic beads or spheres, metal beads or spheres, ceramic (e.g., ceramics, which may include alumina, yttria, and zirconia) or honeycomb materials comprising ceramic and/or metal, other forms of tubes comprising ceramic and/or metal, extruded monoliths and the like. Typically, the thermal mass is selected from among those that substantially maintain integrity (structural and compositions) and functionality during long term exposure to dehydrocyclization feeds, products, and reaction conditions, e.g., temperatures ≥700° C., e.g., ≥800° C., or for increased operating margin ≥1000° C. Regenerative beds, such as those described in U.S. Pat. No. 8,754,276 (incorporated by reference herein in its entirety) are suitable for use as thermal mass, but the invention is not limited thereto. Typically, thermal mass 1 has the form of an elongated ceramic tube having (i) at least one internal channel for conveying the feeds and products through the reaction zone and (ii) opposed openings 3 and 5 in fluidic communication with the internal channel(s). In particular aspects, thermal mass 1 has the form of an elongated honeycomb comprising alumina and/or silica. The honeycombs can be arranged adjacent to one another (e.g., end-to-end, in series). Typically, in these aspects, there is substantial alignment of a segment's internal channels with those of its neighbors to facilitate fluidic communication through all of the segments constituting the thermal mass. The segments can be of substantially the same composition, but this is not required. The reaction zone further comprises at least one active material 14. Active material 14 is selected from among one more of the specified dehydrocyclization catalysts. Typically in these aspects, active material 14 located in one or more of the internal channel(s) of thermal mass 1 or one or more segments thereof. In certain aspects, the inner surface of thermal mass 1 or one or more segments thereof serves as a catalyst support. Optionally, the reaction zone further comprises at least one solid oxygen carrier, or "SOC" (not shown), typically in proximity to the active material. For example, the SOC can be included in thermal mass 1 as coating on the thermal mass's internal surface, such as a coating which includes the specified dehydrocyclization catalyst and the SOC. During regeneration mode, the SOC uptakes (typically by chemical bonding, chemisorption, physisorption, etc., collectively "sorption") an unreacted portion of the oxidant present in the reaction zone to produce a pre-oxidized SOC. During reaction mode, the SOC releases at least a portion of the sorbed oxidant for combustion of molecular hydrogen produced during the dehydrocyclization, resulting in a reduced SOC and an improved aromatic hydrocarbon yield. Since the release of the SOC's sorbed oxidant and the combustion of the released oxidant with molecular hydrogen are typically net exothermic, use of an SOC also makes thermal mass 1 more isothermal during reaction mode, which further increases aromatic hydrocarbon yield. Conventional SOCs can be used, but the invention is not limited thereto. Suitable SOCs are described in U.S. Patent Application Publication No. 2015/0065769 (where they are identified as oxygen storage materials), which is incorporated by reference herein in its entirety. Alternatively or in addition, staged oxygen introduction into the reaction zone (not shown) during reaction mode to accomplish the same purpose.

The internal volume of reactor 50 of FIGS. 1A and 1B also includes a heat transfer zone. The heat transfer zone typically includes at least one thermal mass 7. Unlike the reaction zone, the heat transfer zone typically does not include an active material, e.g., is substantially free of material that is catalytically active for dehydrocyclization of substantially-saturated hydrocarbon. Thermal mass 7 can be selected from among the same thermal masses specified for use as thermal mass 1 (but without a dehydrocyclization catalyst). Typically, thermal mass 7 has the form of an elongated ceramic tube having (i) at least one internal channel for conveying feeds and products through the heat transfer zone and (ii) opposed openings 9 and 11 in fluidic communication with the internal channel(s). As is the case for thermal mass 1, thermal mass 7 can have the form of one or more elongated honeycombs comprising alumina and/or silica. During reaction mode, the heat transfer zone cools the aromatic-containing reaction product (typically gaseous) of the dehydrocyclization, which lessens undesirable thermal side reactions that might otherwise occur if the reaction product is not quenched within the reactor. During regeneration mode, heat is transferred from the heat transfer zone to the fuel and oxidant so that combustion of the fuel and a portion of the oxidant can occur in the third zone and optionally in the reaction zone. It has been found that aromatic hydrocarbon is significantly more resistant to reverse reactions (which undesirably can produce molecules of greater saturation) than is expected from the teachings of U.S. Pat. No. 8,754,276. Accordingly, in certain aspects (not shown) a heat transfer zone is not present in reactor 50 because its quenching function is not needed during reaction mode, and other means such as igniters, fired heaters, etc. can be used for heating the oxidant and fuel to combustion temperature during regeneration mode.

The internal volume of reactor 50 of FIGS. 1A and 1B also includes a third zone, typically a central zone, located between the reaction and heat-transfer zones. The third zone is configured for (i) mixing the fuel and a portion of the oxidant during regeneration mode for efficient combustion, (ii) increasing distribution uniformity over third zone's internal cross sectional area of the combustion products, unreacted oxidant, and optionally unreacted fuel, and (iii) lessening undesirable pressure-drop effects during reaction mode. The third zone can have the form of an open volume within the internal volume of reactor 50, e.g., an open volume having a length L and substantially constant cross-sectional area A. Those skilled in the art will appreciate that an open volume having an appropriate L:A ratio will provide at least some mixing and distribution during regeneration mode without creating too great a pressure drop during reaction mode. More typically, since it provides improved mixing and distribution and allows a lesser overall length for the third zone, the third zone includes at least one mixer-distributor apparatus 10. The mixer-distributor 10, which can have the form of a relatively thin member (e.g., a plate) having one or more orifices effective for carrying out the mixing and distribution during regeneration mode. Generally, the orifices have sufficient cross sectional area to prevent an undesirably large pressure drop across the third zone during reaction mode. Conventional mixer-distributors can be used, such as those described in U.S. patent application Publication Ser. No. 13-015,7205 A1 and U.S. Pat. No. 7,815,873 (incorporated by reference herein in their entireties), but the invention is not limited thereto. Optionally, the third zone contains at least one selective combustion catalyst. Suitable selective combustion catalysts are described in U.S. Pat. No. 8,754,276, but the invention is not limited thereto. When used, a fixed bed of the selective combustion catalyst can be included as a component of mixer-distributor 10, e.g., with one or more of the mixer-distributor's plate members serving as a catalyst support. Alternatively or in addition, a bed of the selective combustion catalyst can be located in the third zone, e.g., between mixer-distributor 10 and the reaction zone.

Combustion of fuel and oxidant can be carried out in a location other than within the internal volume of reactor 50. For example, the fuel combustion can be carried out at a location external to reactor 50, with the combustion products, unreacted oxidant, and optionally unreacted fuel being conveyed to the vicinity of active material 14 for (i) heating the reaction zone to a temperature sufficient for efficiently carrying out catalytic dehydrocyclization, (ii) combusting catalyst coke deposits with at least a portion of the unreacted oxidant, and optionally (iii) replenishing SOC oxidant content when an SOC is present in the reaction zone. Accordingly, in certain aspects (not shown) reactor 50 does not include the third zone. In other aspects (also not shown), reactor 50 includes neither the heat transfer zone nor the third zone.

The dehydrocyclization reaction is carried out in a preheated reaction zone. Continuing with reference to FIG. 1A, at the start of reaction mode, the vicinity of opening 5 is at an elevated temperature as compared to that at the vicinity of opining 3. Although the temperature profile across thermal mass 1 can monotonically increase across thermal mass 1 from opening 3 to opening 5, as in the aromatization of U.S. Pat. No. 8,754,276, this is not required. For example, in certain aspects, e.g., when the feed includes ≥50 wt. % ethane and a relatively brief reaction mode time duration is used to boost ethane conversion, a lesser amount of coke is deposited in the vicinity of the active material 14 during reaction mode. In these aspects, heat generated by coke combustion during regeneration mode may be insufficient to move the temperature profile's peak from the third zone to the reaction zone. In other aspects, e.g., when the feed comprises ethane and ≥50 wt. % of $C_{3+}$ hydrocarbon, and relatively severe dehydrocyclization conditions are used for a longer duration, a greater amount of coke is deposited in the vicinity of active material 14. In these aspects, heat generated by coke combustion during regeneration mode may be sufficient to move the temperature profile's peak from the third zone to the reaction zone.

An example of a suitable temperature profile at the start of reaction mode is shown in FIG. 1A. The profile indicates a temperature at the inward end of active material 14 that is less than the peak temperature, which is within the reaction zone. The temperature at the outward end of active material 14 is less than both the peak temperature and the temperature at the inward end of active material 14, with inward and outward being with respect to the center of reactor 50. The invention is not limited to the temperature profile of FIG. 1A. Examples of other suitable temperature profiles at the start of reaction mode include those (i) having no pronounced peak, (ii) having a peak in the third zone, (iii) having a first peak in the third zone and a second peak in the reaction zone (the second peak being less than, greater than, or substantially the same as the first peak's temperature, and (iv) having a temperature at the inward end of active material 14 that is less than or the same as the temperature at the outward end. The greatest temperature achieved in the reaction zone at the start of reaction mode (e.g., the peak temperature of FIG. 1A) is typically less than or equal to maximum temperature specified for the desired dehydrocyclization reaction. Likewise, the least temperature achieved in the reaction zone at the start of reaction mode (e.g., the temperature indicated at the outward end of active material 14 in FIG. 1A) is typically greater than or equal to the minimum temperature specified for the desired dehydrocyclization reaction. It has been found that an improvement in feed conversion can be archived during dehydrocyclization with improved aromatic hydrocarbon yield and a lesser yield of coke deposits when the temperature profile across the extent of active material 14 is more isothermal, e.g., by decreasing excursions in the temperature profile away from the reaction zone's average temperature in the vicinity of active material 14. Making the reaction zone more isothermal during reaction mode has been found to decrease selectivity to catalyst coke. Beneficially, this allows for a shortened duration of regeneration mode in aspects where more time is needed for removing coke deposits than for reactor reheating. Conventional temperature measurements can be used to determine the average temperature of active material 14. For example, when active material has a substantially uniform density and cross-sectional area from its inward end to its outward end, the average temperature across active material 14 can be obtained by summing the temperature of active material 14 at each of ten or more substantially equally-spaced points from the inward end of active material to the outward end of active material 14, and then dividing the sum by the number of points. Optionally, deviations from the average temperature across active material 14 from the inward end to the outward end at the start of reaction mode do not exceed (i) the maximum temperature indicated for the desired dehydrocyclization reaction and (ii) +/−25% of the average temperature (in degrees Celsius), e.g., +/−15%, such as +/−10%, or +/−5% (substantially isothermal). Typically, the reverse-flow reactor's temperature profile does not remain substantially constant as reaction mode progresses from start to finish. For example, as shown in FIG. 1A, the temperature profile's leading edge 4 and trailing edge 2 move toward the third zone as reaction mode progresses. Use of an SOC proximate to active material 14 or included as a component of the active material can make the reaction zone more isothermal. The combination of oxidant release from the SOC and combustion of at least a portion of the reaction product's molecular hydrogen with the released oxidant is typically net exothermic, which can offset the endothermic dehydrocyclization. This effect can alter the shape of the reactor's temperature profile in the reaction zone, e.g., by increasing the temperature (not shown) of the trailing edge 2. The same alteration can be achieved by intruding an oxidant stream at one or more locations proximate to active material 14 during reaction mode. Since water can deactivate certain dehydrocyclization catalysts and can cause dealumination of certain molecular sieves, the amount of oxidant introduced into the reaction zone during reaction mode is typically equal to or less than the amount needed to consume ≤90% of the reaction product's molecular hydrogen, e.g., ≤50%.

Certain aspects of reaction mode operation will now be described with continued reference to FIG. 1A. The invention is not limited to these aspects, and this description is not meant to foreclose other reaction modes within the broader scope of the invention. Referring to FIG. 1A, at least one of the specified feeds is conducted to reverse-flow reactor 50 via conduit 15. The feed enters thermal mass 1 via opening 5, and the feed is heated by a transfer of heat from pre-heated thermal mass 1. The heated feed contacts active material 14 and endothermically reacts under catalytic dehydrocyclization conditions, resulting in coke deposits in the vicinity of active material 14 and the production of a reaction product comprising aromatic hydrocarbon and molecular hydrogen. The reaction product exits the reaction zone 1 through opening 5 at an elevated temperature and passes into pre-cooled second thermal mass 7 through opening 11. As the reaction product passes through the second thermal mass 7, the reaction product transfers heat to the thermal mass. This serves at least two functions: (i) the heat transfer quenches (cools) the reaction production, which lessens undesired thermal reactions, and (ii) the heat transfer readies the thermal mass for subsequent regeneration mode operation. Quenched reaction product exits thermal mass 7 at opening 9, and is conducted away from the reverse flow reactor via aperture 52, e.g., for recovery of aromatic hydrocarbon. Although reaction mode can be carried out so long as catalytic dehydrocyclization conditions subsist at one or more location in active material 14 that is in contact with the feed, it is typical to use a shorter time duration. For example, it has been found that improved feed conversion is achieved when reaction mode time duration is ≤60 seconds, e.g., ≤30 seconds, such as ≤10 seconds, or ≤1 second, or ≤0.1 second. For example, reaction mode can be carried out for a time duration in the range of from 0.01 seconds to 30 seconds, or 0.1 seconds to 10 seconds, e.g., 0.1 seconds to 5 seconds, such as 0.1 seconds to 1.5 seconds. While not wishing to be bound by any theory or model, it is believed that the benefit of a shortened reaction mode time duration results from the nature of coke deposited on or in the specified dehydrocyclization catalyst during reaction mode operation. It is observed for the specified dehydrocyclization catalysts of active material 14 that catalytic dehydrogenation of the feed's substantially non-aromatic hydrocarbon occurs mainly on or near the catalyst's surface. In contrast to this, is observed that cyclization of the unsaturated fragments occurs mainly in the pores of the dehydrocyclization catalyst's molecular sieve component. Since those pores are small and are easily blocked by coke depicts, cyclization reactions are curtailed by even moderate coke accumulation. Although cyclization can be inhibited by even moderate coke accumulation, dehydrogenation reactions such as those disclosed in U.S. Pat. No. 8,754,276, typically continue with at least some yield of their desired unsaturated product. Accordingly, operating reaction mode for a time duration of 90 seconds or less before commencing regeneration has been found to provide for both substantial dehydrogenation and substantial cyclization in the vicinity of active material 14.

At the end of reaction mode, and following any other processing (e.g., sweep gas flow), the reactor is ready for regeneration mode. FIG. 1B shows one representative temperature profile as may exist in the reactor at the start of regeneration mode. Previous reaction mode operation (an optional additional processing, if used) has resulted in a relocation of the temperature profile's peak at the start of regeneration mode to a position in the third zone that is proximate to the heat transfer zone. Reactor heating during regeneration mode is primarily from fuel combustion in the third zone and catalyst coke combustion in the reaction zone, but also optionally fuel combustion in the reaction zone. Over the course of regeneration mode operation, this heating has the effect of translating the temperature profile's leading edge 6 and trailing edge 8 toward the reaction zone, as shown in FIG. 1B.

During regeneration mode, oxidant is conducted in reverse-flow toward reverse flow reactor 50 via one or more conduits 19. Typically, one or more additional conduits (not shown) are used for conducting fuel to reactor 50 for combustion with a portion of the oxidant. Typically in the aspects illustrated in FIG. 1B, the fuel is also conducted to the reactor in reverse-flow, but other fuel flow directions are within the scope of the invention. Fuel and oxidant are introduced into reactor 50 via aperture 52, and these streams continue in reverse-flow toward thermal mass 7. These streams enter thermal mass 7 through opening 9, and are typically conveyed through thermal mass 7 via separate channels that are not in fluidic communication with one another. This lessens or substantially prevents combustion in the heat transfer zone. Heat is transferred from thermal mass 7 to the fuel and the oxidant, which brings the fuel and oxidant closer to their combustion temperature and re-cools thermal mass 7. Heated fuel and a first portion of the heated oxidant exiting opening 11 of thermal mass 7 combust in the third zone. Optionally, the combustion is aided by a mixer-distributor apparatus and/or by a selective combustion catalyst. This combustion produces heat and a first combustion product. Un-combusted oxidant, the first combustion product, and any unreacted fuel are conducted into thermal mass 1 via opening 5. At least a portion of the un-combusted oxidant combusts in the vicinity of active material 14 with at least a portion of accumulated catalyst coke deposits, and optionally with at least a portion of any uncommuted fuel to produce a second combustion product. Typically the first and second combustion products combine in the reaction zone to produce a combustion effluent. The combustion effluent, any un-combusted fuel, and any un-combusted oxidant are conducted away from thermal mass 1 via opening 3, and then out of reactor 50 via aperture 51 and conduit 45. When an SOC is present in the reaction zone, a portion of the un-combusted oxidant can be sorbed by the SOC for release during a reaction mode. Heat is transferred to the reaction zone as a result of at least (i) the heat transferred to the fuel and oxidant in the heat transfer zone, (ii) combustion in the third zone, and (iii) the combustion of coke deposits in the reaction zone. At the end of regeneration mode, the regenerated reverse-flow reactor 50 can have, e.g., the temperature profile indicated in FIG. 1A.

Generally, ≥25 wt. % (but less than all) of the oxidant provided during regeneration mode is combusted with the fuel, e.g., ≥50 wt. %, such as ≥75 wt. %, or ≥90 wt. %, or in the range of from 50 wt. % to 95 wt. %, or 55 wt. % to 90 wt. %. Typically, the amount of oxidant that is not combusted with the fuel is in the range of from 0.1 wt. % to 20 wt. %, e.g., 0.1 wt. % to 10 wt. %, the weight percents being based on the weight of the oxidant provided during regeneration mode.

Generally, ≥25 wt. % of the remainder of the oxidant (un-combusted oxidant remaining after fuel combustion) combusts accumulated coke deposits in reactor 50, e.g., those in the reaction zone, and particularly those vicinity of active material 14 (catalyst coke deposits). Typically, ≥50 wt. % of the remainder of the oxidant is consumed combusting catalyst coke deposits, such as ≥75 wt. %, or ≥90 wt. %, or in the range of from 50 wt. % to 95 wt. %, or 55 wt. % to 90 wt. %. Optionally, ≥50 wt. % of the fuel provided for regeneration mode is combusted in the reactor. This is typically the case when the reverse-flow reactor includes the specified third and/or heat transfer zones. For example, ≥75 wt. % of the fuel provided for regeneration mode can be consumed in the third zone, such as ≥90 wt. %, or ≥95 wt. %. In certain aspects, some fuel is reserved for combustion in the reaction zone, e.g., in order to make the reaction zone more isothermal.

Examples of substantially-saturated $C_{2+}$ hydrocarbon feeds, dehydrocyclization catalysts, dehydrocyclization conditions, fuels, oxidants, and regeneration conditions for carrying out certain aspects of the invention will now be described in more detail. This description is not meant to foreclose the use of other feeds, fuels, oxidants, and process conditions within the broader scope of the invention.

Representative Feeds

The feed typically comprises one or more $C_2$ to $C_9$ non-aromatic hydrocarbon compounds, e.g., one or more light hydrocarbon (i.e., $C_2$ to $C_5$) compounds, such as one or more paraffinic light hydrocarbon compounds. For example, the feed can comprise ≥1 wt. % based on the weight of the feed of one or more of (i) paraffinic $C_2$ to $C_9$ hydrocarbon, (ii) aliphatic $C_2$ to $C_9$ hydrocarbon, (iii) aliphatic paraffinic $C_2$ to $C_9$ hydrocarbon, (iv) paraffinic light hydrocarbon, (v) aliphatic light hydrocarbon, and (vi) aliphatic paraffinic light hydrocarbon; such as ≥10 wt. %, or ≥25 wt. %, or ≥50 wt. %, or ≥75 wt. %, or ≥90 wt. %, or ≥95 wt. %. Optionally, the feed further comprises diluent. Diluent present in the feed's source (e.g., methane and/or $CO_2$ present in natural gas) and diluent added to the feed are within the scope of the invention. Diluent, when present, is typically included in the feed in an amount ≤60 wt. % based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified dehydrocyclization catalyst, e.g., methane, molecular nitrogen, and inert atomic gasses such as argon.

The feed typically contains $C_3$ and/or $C_4$ hydrocarbon e.g., (i) ≥20 wt. % propane, such as ≥40 wt. %, or ≥60 wt. %, and/or (ii) ≥20 wt. % butanes, such as ≥40 wt. %, or ≥60 wt. %. Although the feed can contain $C_{5+}$ hydrocarbon, the amount of $C_{5+}$ hydrocarbon when present is typically small, e.g., ≤20 wt. %, such as ≤10 wt. %, or ≤01 wt. %. Typically, the feed contains ≤10 wt. % of $C_{6+}$ saturated hydrocarbon, e.g., ≤5 wt. %.

The feed can contain methane, e.g., ≥1 wt. % methane, such as ≥10 wt. %, or ≥20 wt. %, or ≥60 wt. %. Even though methane is a diluent, i.e., it typically does not react to produce aromatic hydrocarbon or catalyst coke in the presence of the specified dehydrocyclization catalyst under the specified reaction conditions, its presence is beneficial. It is believed that this benefit results at least in part from a decrease in the partial pressure of the feed's $C_2$-$C_9$ hydrocarbon, which lessens the amount of catalyst coke formed under the specified dehydrocyclization process conditions. Typically, the feed comprises a total of ≤10 wt. % of impurities such as CO, $CO_2$, $H_2S$, and total mercaptan; e.g., ≤1 wt. %, or ≤0.1 wt. %. Optionally, the feed comprises molecular hydrogen, e.g., ≥1 wt. % molecular hydrogen based on the weight of the feed, such as ≥5 wt. %. One representative feed comprises (i) ≥10 wt. % ethane, such as in the range of from 10 wt. % to 40 wt. %; and further comprises (ii) 1 wt. % to 40 wt. % methane, (iii) 20 wt. % to 50 wt. % propane, and (iv) 20 wt. % to 50 wt. % butanes.

Optionally, the feed contains unsaturated $C_{2+}$ hydrocarbon, such as $C_2$-$C_5$ unsaturated hydrocarbon. When present, the amount of $C_{2+}$ unsaturated hydrocarbon is typically ≤20 wt. %, e.g., ≤10 wt. %, such as ≤1 wt. %, or ≤0.1 wt. %, or in the range of from 0.1 wt. % to 10 wt. %. Typically, the feed is substantially-free of non-aliphatic hydrocarbon. More particularly, the feed can be substantially-free of aromatic hydrocarbon, where substantially-free in this context means <1 wt. % based on the weight of the feed, such as ≤0.1 wt. %, or ≤0.01 wt. %, or ≤0.001 wt. %.

The feed's light hydrocarbon can be obtained from one or more sources of hydrocarbon, e.g., from natural hydrocarbon sources including those associated with producing petroleum, or from one or more synthetic hydrocarbons sources such as catalytic and/or non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feed can include recycle components, e.g., a portion of the second product. Such recycle, when used, can include, e.g., methane, molecular hydrogen, and $C_{2+}$ hydrocarbon, typically $C_2$ to $C_5$ hydrocarbon.

In certain aspects, the source of light hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be one that is obtained by conventional production methods but the invention is not limited thereto. Raw natural gas is a natural gas obtained from a geologic formation without intervening processing. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |

TABLE 1-continued

| Component | Associated Gas | Dry Gas | Condensate Well Gas |
|---|---|---|---|
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.1-1 (0.09) |

In certain aspects, the feed comprises ≥75 wt. % Associated Gas, based on the weight of the feed, e.g., ≥90 wt. %, or ≥95 wt. %. Associated Gas is typically found with petroleum deposits, e.g., dissolved in the oil or as a free "gas cap" above the oil in a reservoir. Since methane is not detrimental to the process, and is in at least some aspects beneficial, the invention obviates the need for costly and inefficient cryogenic methane separation facilities, such as one or more conventional cold boxes. The invention is particularly advantageous for upgrading relatively refractory paraffinic hydrocarbon such as ethane. Accordingly, the feed can comprise ethane in an amount ≥1 wt. %, e.g., ≥5 wt. %, such as ≥10 wt. %. Suitable feeds include those comprising >50 wt. % ethane, such as ≥75 wt. %, or ≥90 wt. %, or ≥95 wt. %. For example, the feed can comprise an amount of ethane in the range of from 1 wt. % to 99 wt. %, such as 5 wt. % to 95 wt. %, or 10 wt. % to 90 wt. %. One representative feed comprises (i) ≥10 wt. % ethane, or ≥50 wt. %, or ≥90 wt. %, such as in the range of from 10 wt. % to 99.5 wt. % ethane, with ≥95 wt. % of the balance of the feed comprising one or more of methane, propane, and butanes.

The specified feed is exposed to an active material which includes at least one of the specified the dehydrocyclization catalysts during reaction mode operation in a reverse-flow reactor. Certain aspects of the dehydrocyclization catalyst will now be described in more detail. The invention is not limited to these aspects, and this description is not meant to foreclose other aspects of the dehydrocyclization catalyst within the broader scope of the invention.

Representative Dehydrocyclization Catalysts

Typically, the dehydrocyclization catalyst includes ≥10 wt. % of the molecular sieve component and ≥0.005 wt. % of the dehydrogenation component, wherein the molecular sieve component has a Constraint Index in the range of from 1-12, and the dehydrogenation component comprises one or more elements selected from Groups 3 to 13 of the Periodic Table. When the molecular sieve component and dehydrogenation component together include less than 100 wt. % of the catalyst, ≥90 wt. % of the remainder of the catalyst can include a matrix component, such as ≥99 wt. % of the remainder.

The catalyst typically includes the molecular sieve component in an amount ≥20 wt. %, based on the weight of the catalyst, e.g., ≥25 wt. %, such as ≥50 wt. %, or in the range of from 30 wt. % to 99.9 wt. %. In certain aspects, the molecular sieve component includes aluminosilicate, e.g., ≥90 wt. % of at least one aluminosilicate. The aluminosilicate can be an un-substituted aluminosilicate, a substituted aluminosilicate, or a combination thereof. For example, the aluminosilicate can be in a form where at least a portion of its original metal has been replaced, e.g., by ion exchange, with other suitable metal (typically metal cation) of Groups 1-13 of the Periodic Table. Typically, the aluminosilicate includes zeolite aluminosilicate, e.g., ≥90 wt. % of at least one zeolite based on the weight of the aluminosilicate. The term zeolite includes those in which at least part of the aluminum is replaced by a different trivalent metal, such as gallium or indium.

The molecular sieve component typically includes ≥90 wt. % of one or more of the specified molecular sieves, e.g., ≥95 wt. %. In certain aspects, the molecular sieve component includes at least one zeolite molecular sieve, e.g., ≥90 wt. % zeolite, such as ≥95 wt. %, based on the weight of the molecular sieve component. The molecular sieve component can consist essentially of zeolite, consist of zeolite, or can include zeolite in combination with other (e.g., non-zeolitic) molecular sieve. The zeolite can be in hydrogen form, e.g., zeolite synthesized in the alkali metal form and then converted to the hydrogen form. Typically the zeolite has a medium pore size and a Constraint Index of 2-12 (as defined in U.S. Pat. No. 4,016,218). Optionally, the zeolite has at least one set of pores of substantially uniform size extending through the molecular sieve, wherein geometric mean of the cross-sectional dimensions of each of the sets of pores is ≥5 Å, or ≥5.3 Å, e.g., ≥5.4 Å such as ≥5.5 Å, or in the range of 5 Å to 7 Å, or 5.4 Å to 7 Å. Examples of suitable zeolites include ZSM-5 (including H-ZSM-5), ZSM-11, ZSM-12, ZSM-22, ZSM-23, ZSM-35, and ZSM-48, including and mixtures and intermediates thereof such as ZSM-5/ZSM-11 admixture. For example, the molecular sieve component can include ≥90 wt. % of (A) ZSM-5 and/or (B) ZSM-12, based on the weight of the molecular sieve component, e.g., ≥95 wt. % of H-ZSM-5. In certain aspects, the molecular sieve has a relatively small crystal size, e.g., small crystal ZSM-5, meaning ZSM-5 having a crystal size ≤0.05 micrometers (μm), such as in the range of 0.02 μm to 0.05 μm. Small crystal ZSM-5 and the method for determining molecular sieve crystal size are disclosed in U.S. Pat. No. 6,670,517, which is incorporated by reference herein in its entirety.

In other aspects, the molecular sieve component includes at least one molecular sieve of the MCM-22 family (including mixtures of MCM-22 family molecular sieve), e.g., MCM-22 alone or in combination with other molecular sieve such as one or more of the specified zeolites. The MCM-22 family includes those molecular sieves having an X-ray diffraction pattern including d-spacing maxima (in Å) at 12.4±0.25, 6.9±0.15, 3.57±0.07 and 3.42±0.07. Examples of suitable MCM-22-family molecular sieve include PSH-3, SSZ-25, ITQ-1, MCM-36, MCM-49, MCM-56, UZM-8, ERB-1, and ITQ-2.

When the molecular sieve component includes at least one aluminosilicate, the aluminosilicate's silica:alumina ratio (substantially the same as the aluminosilicate's $Si:Al_2$ atomic ratio) is typically ≥2, e.g., in the range of from 5 to 100. The silica:alumina ratio is meant to represent the $Si:Al_2$ atomic ratio in the rigid anionic framework of the crystalline aluminosilicate. Alternatively or in addition, the catalyst can be made more resistant to deactivation (and increase aromatic hydrocarbon yield) by including phosphorous with the molecular sieve component. When used, the amount of phosphorous is typically ≥1 wt. % based on the weight of the molecular sieve component. For example, when the molecular sieve component includes aluminosilicate, the phosphorous:aluminum atomic ratio can be in the range of from 0.01 to 1. Zeolite having a higher silica:alumina ratio provide a lower catalyst acidity, e.g., in the range of from 44 to 100, such as 50 to 80, or 55 to 75. When the aluminosilicate includes phosphorous, the phosphorous:aluminum atomic ratio is typically in the range of from 0.01 to 0.5. For example, the catalyst can contain ≥10 wt. % of phosphorous-modified alumina, such as ≥15 wt. %, or in the range of from 10 wt. % to 20 wt. %.

In addition to the molecular sieve component, the catalyst includes ≥0.005 wt. %, based on the weight of the catalyst, of a dehydrogenation component, e.g., at least one dehydrogenation metal. The dehydrogenation component can include one or more neutral metals selected from Groups 3 to 13 of the Periodic Table, such as one or more of Ga, In, Zn, Cu, Re, Mo, W, La, Fe, Ag, Pt, and Pd, and/or one or more oxides, sulfides and/or carbides of these metals. For example, the dehydrogenation component can be Ga, Zn, or a combination thereof, optionally supported on a catalyst including ZSM-5 as the molecular sieve component.

Typically, the dehydrogenation component includes ≥90 wt. % of the one or more of the specified dehydrogenation metals and/or oxide thereof, e.g., ≥95 wt. %, or ≥99 wt. %. For example, the dehydrogenation component can include ≥90 wt. % of (A) Ga and/or (B) Zn, including oxides thereof. Typically, the catalyst includes ≥0.01 wt. % of the dehydrogenation component, based on the weight of the catalyst, e.g., ≥0.1 wt. % of the dehydrogenation component, such as ≥0.5 wt. %, or ≥1 wt. %.

Those skilled in the art will appreciate that when the dehydrogenation component includes one or more metals of greater catalytic dehydrogenation activity, e.g., Pt, and/or Pd, a lesser amount of dehydrogenation component is needed, e.g., in the range of 0.005 wt. % to 0.1 wt. %, based on the weight of the catalyst, such as 0.01 wt. % to 0.6 wt. %, or 0.01 wt. % to 0.05 wt. %. When the dehydrogenation component includes one or more metals of lesser dehydrogenation activity, e.g., one or more of Ga, In, Zn, Cu, Re, Mo, and W, a greater amount of dehydrogenation component is needed, e.g., in the range of 0.05 wt. % to 10 wt. %, based on the weight of the catalyst, such as 0.1 wt. % to 5 wt. %, or 0.5 wt. % to 2 wt. %.

The dehydrogenation component can be provided on, in, or proximate to the catalyst in any manner, for example by conventional methods such as impregnation or ion exchange. At least part of the dehydrogenation metal may also be present in the crystalline framework of the molecular sieve. For one representative catalyst, (i) the dehydrogenation component includes ≥95 wt. % of (A) Ga and/or (B) Zn, and (ii) the molecular sieve component includes ≥95 wt. % of H-ZSM-5.

In certain aspects, the dehydrogenation component includes ≥99 wt. % of one or more of Ga, Zn, and In, and the molecular sieve component includes ≥99 wt. % of ZSM-5-type zeolite that has been impregnated with the dehydrogenation metal component and/or ion exchanged with the dehydrogenation metal component. For example, the catalyst can include Ga-impregnated and/or In-impregnated H-ZSM-5, Ga-exchanged and/or In-exchanged H-ZSM-5, H-gallosilicate of ZSM-5 type structure and H-galloaluminosilicate of ZSM-5 type structure. Optionally, the catalyst includes (i) tetrahedral aluminum and/or gallium, which is present in the zeolite framework or lattice, and/or (ii) octahedral gallium or indium, which is not present in the zeolite framework but present in the zeolite channels in close vicinity to the zeolitic protonic acid sites. While not wishing to be bound by any theory or model, the tetrahedral or framework Al and/or Ga is believed to contribute to acid function of the catalyst and octahedral or non-framework Ga and/or In is believed to contribute to the dehydrogenation function of the catalyst. Although typically the zeolite is impregnated or ion-exchanged with the dehydrogenation metal, other forms of zeolite can be used, such as H-galloaluminosilicate of ZSM-5 type structure having framework (tetrahedral) Si/Al and Si/Ga atomic ratios of about 10:1 to 100:1 and 15:1 to 150:1, respectively, and non-framework (octahedral) Ga of about 0.5 wt. % to 0 wt. %.

Besides the molecular sieve component and dehydrogenation component, the catalyst can further include an optional matrix component, e.g., one or more inorganic binders. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titania, magnesia or mixtures of these and other oxides. The matrix component can include naturally occurring materials and/or materials in the form of gelatinous precipitates or gels including mixtures of silica and metal oxides. Clays may also be included with the oxide type binders for improved mechanical properties or ease of manufacture.

Alternatively or in addition, the matrix component can include one or more substantially inactive materials. Inactive materials suitably serve as diluents to control the amount of conversion so that products may be obtained economically and orderly without employing other means for controlling the rate of reaction. Alternatively or in addition to any phosphorous added to or impregnated into the molecular sieve component, the matrix component can optionally include phosphorous, e.g., to lessen catalyst acidity. Those skilled in the art will appreciate that lessening catalyst acidity decreases the amount of catalyst coke produced during the catalytic conversion of the feed's light hydrocarbon to aromatic hydrocarbon. Suitable phosphorous-containing matrices are disclosed in U.S. Pat. No. 5,026,937, which is incorporated by reference herein in its entirety. The matrix component is optional. In certain aspects, the catalyst is substantially-free of matrix, e.g., contains ≤1 wt. % of matrix, such as ≤0.1 wt. %. In particular, the catalyst can be substantially free of binder, e.g., contains ≤1 wt. % of binder, such as ≤0.1 wt. %. For example, the catalyst's molecular sieve component can includes ≥95 wt. % of substantially binder-free bound molecular sieve, e.g., ≥95 wt. % of substantially binder-free ZSM-5, and in particular small crystal H-ZSM-5.

The dehydrocyclization catalyst can be subjected to one or more treatments, e.g., a selectivation treatment to increase selectivity for producing desired aromatic hydrocarbon compounds such as para-xylene. For example, the selectivation can be carried out before introduction of the catalyst into the reactor and/or in-situ in the reactor, e.g., by contacting the catalyst with a selectivating agent, such as at least one organosilicon in a liquid carrier and subsequently calcining the catalyst at a temperature of 350° C. to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047.

In particular aspects, e.g., those where it is desired to convert <50 wt. % of any feed ethane, the dehydrocyclization catalyst (Catalyst A) has a molecular sieve component which includes ≥90 wt. % of an aluminosilicate in hydrogen form, the aluminosilicate having a constraint index in the range of from 2-12 (e.g., phosphorous-modified H-ZSM-5) and a silica to alumina ratio in the range of from 50 to 80. For example, the molecular sieve component can include ≥95 wt. % of substantially binder-free, small crystal H-ZSM-5. For Catalyst A, the dehydrogenation component can include ≥90 wt. % of at least one oxide of Ga. The matrix component, when used, can include ≥75 wt. % of alumina, silica, and combinations thereof. Catalyst A optionally includes ≥1 wt. % phosphorus, e.g., in the form of phosphorous-modified H-ZSM-5 and/or by including phosphorous in the matrix component.

In other aspects, e.g., those where it is desired to convert ≥50 wt. % of the feed's ethane, the dehydrocyclization catalyst (Catalyst B) typically has greater acidity than that of Catalyst A. For Catalyst B, the molecular sieve component can include ≥90 wt. % of an aluminosilicate in hydrogen form, the aluminosilicate having a constraint index in the range of from 2-12 (e.g., small crystal, H-ZSM-5). Typically, the dehydrocyclization catalyst of Catalyst B has (i) a silica:alumina ratio in the range of from 3 to 60, e.g., from 10 to 40, such as from 15 to 35, and (ii)<0.01 wt. % phosphorus. It is also typical for Catalyst B's dehydrogenation component to include ≥90 wt. % of (i) at least one oxide of Zn and/or (ii) at least one oxide of Ga, such as ≥95 wt. % of at least one oxide of Zn. The matrix component when used includes ≥90 wt. % of alumina, silica, and combinations thereof.

The specified dehydrocyclization catalysts can have any form that is convenient for use as active material in the reverse-flow reactor. For example, the dehydrocyclization catalyst can be in the form of a coating on or in the internal volume of a thermal mass located in the reverse-flow reactor's reaction zone. Alternatively or in addition, the dehydrocyclization catalyst can be in the form of a composite with the thermal mass. The thermal mass can include both the specified SOC and the dehydrocyclization catalyst, e.g., as a coating on the internal surface of the thermal mass. The coating can be formed by conventional methods, e.g., by applying a coating mixture continuing the SOC (or precursors thereof) and the dehydrocyclization catalyst (or precursors thereof) and then processing (typically controlled heating) the thermal mass and applied mixture to form the coated thermal mass.

Representative Reaction Mode Conditions

The dehydrocyclization reaction can be carried out in the reverse-flow reactor's reaction zone by exposing the feed to a catalytically effective amount of one or more of the specified dehydrocyclization catalysts during reaction mode. Representative conditions within the reaction zone during reaction mode typically include a maximum temperature ≤750° C., e.g., ≤700° C., such as ≤650° C.; an average temperature within the reaction zone's catalytic region (e.g., within the region occupied by active material 14 in FIG. 1A) in the range of from 400° C. to 700° C., e.g., 400° C. to 650° C.; a pressure ≥10 psia (68.9 kPa), e.g., 0 psig (101 kPa) to 300 psig (2170 kPa); and a space velocity (GHSV) ≥500 hr$^{-1}$, e.g., ≥1100 hr$^{-1}$, such as in the range of from 1500 hr$^{-1}$ to 40,000 hr$^{-1}$. The specified pressure is the pressure at the reaction zone's inlet, not the average pressure. Typical process conditions include an average temperature in range of from 430° C. to 675° C., e.g., 450° C. to 650° C.; a pressure in the range of from 20 psia (137.9 kPa) to 300 psig (2170 kPa), e.g., from 30 psia (207 kPa) to 80 psia (522 kPa); a space velocity (GHSV) in the range of from 2000 hr$^{-1}$ to 20,000 hr$^{-1}$, e.g., 2500 hr$^{-1}$ to 15,000 hr$^{-1}$.

In comparison with conventional processes, the reaction is capable of increased conversion of $C_{2+}$ hydrocarbon without a significant decrease in the selectivity for aromatic hydrocarbon, and without excessive selectivity for light hydrocarbon compounds such as methane. For example, aromatic hydrocarbon selectivity is typically ≥30 wt. %, e.g., ≥40 wt. %, such as ≥50 wt. %, or ≥60 wt. %. Methane selectivity is typically ≤40 wt. %, e.g., ≤30 wt. %, such as ≤20 wt. %. $C_{2+}$ paraffin selectivity is typically ≤5 wt. %, e.g., ≤1 wt. %. $C_{2+}$ olefin selectivity is typically ≤20 wt. %, e.g., ≤10 wt. %. Advantageously, the process exhibits high $C_{2+}$ conversion with low selectivity for methane over a wide range of conversion values. For example, the reaction can achieve (A) a $C_{2+}$ hydrocarbon conversion of X wt. % and (B) a methane selectivity of Y wt. %, wherein when (A) X>60, then Y≤40, (B) X is in the range of 50 to 60 then Y≤20, and (C) X<50 then Y≤15. For example, the process can have an aromatic hydrocarbon selectivity ≥40 wt. % and a methane selectivity ≤40 wt. %. Very large $C_{2+}$ hydrocarbon conversion can be achieved compared to conventional processes, and in particular very large ethane conversion can be achieved. For example, when operating the process under the specified conditions with the specified dehydrocyclization catalyst, $C_{2+}$ conversion (e.g., the $C_2$-$C_4$ paraffinic hydrocarbon conversion, and in particular ethane conversion) is typically ≥65 wt. %, e.g., ≥70 wt. %, such as ≥75 wt. %, or ≥80 wt. %, or in the range of from 65 wt. % to 95 wt. %. The greatest conversion is typically achieved when reaction mode is carried out for a time duration of 90 seconds or less. Typically, the product has a total aromatic hydrocarbon content of ≥5 wt. %, based on the weight of the product, such as ≥10 wt. %, or in the range of from 1 wt. % to 95 wt. %, or 10 wt. % to 75 wt. %. The process produces a desirable BTX product, typically having an increased yield of desirable xylene isomers and a decreased yield of less desirable $C_{11+}$ aromatic hydrocarbon in comparison with conventional processes.

Any convenient method can be employed for recovery of aromatic hydrocarbon from the product, including conventional methods such as boiling point separation, gravity separation, solvent extraction, etc. Non-aromatic $C_{2+}$ hydrocarbon is optionally recovered from the product, e.g., for recycle as a feed component. Methane and/or molecular hydrogen can also be recovered from the product, e.g., for storage, further processing, and/or use as a fuel. The process is compatible with further processing of the recovered aromatic hydrocarbon, e.g., methanation of toluene and/or successive methanation of benzene to produce xylene such as paraxylene.

Representative Regeneration Mode Conditions

Regeneration mode accomplishes at least (i) reheating the reaction zone to establish a reaction zone temperature profile that is sufficient for carrying out subsequent reaction mode operation, e.g., to establish a temperature profile similar to that shown in FIG. 1A, and (ii) removing sufficient coke deposits from the vicinity of dehydrocyclization catalyst in the reaction zone so that during reaction mode both a satisfactory feed conversion and a satisfactory aromatic hydrocarbon yield can be achieved. Regeneration mode is carried out for a time duration sufficient to accomplish both (i) and (ii). When the reactor includes a heat transfer zone, regeneration mode can also accomplish re-cooling the heat transfer zone for reaction product quenching during subsequent reaction mode operation.

In those aspects where the combustion of coke deposits in the reaction zone proceeds more rapidly than reactor reheating, the minimum time duration for regeneration mode is the amount of time needed under regeneration conditions (combustion conditions) for the reaction zone to abstract sufficient heat from the coke combustion, fuel combustion, and any direct or indirect heat transfers (e.g., from the heat transfer zone) to provide a reactor temperature profile suitable for carrying out the specified dehydrocyclization in a subsequent reaction mode. In those aspects where the reactor reheating proceeds more rapidly than the combustion of coke deposits in the reaction zone, the minimum time duration for regeneration mode is the amount of time needed under regeneration conditions which remove sufficient catalyst coke deposits for carrying out the specified dehydrocyclization in a subsequent reaction mode. In these aspects, the minimum time duration of regeneration mode is the time needed to accomplish removal of ≥50.0 wt. %, e.g., ≥75.0 wt. %, such as ≥90.0 wt. %, of accumulated coke deposits in catalytic regions of the reaction zone. Generally, the time duration of regeneration mode is ≤500 seconds, e.g., ≤100 seconds, such as ≤10 seconds, or ≤1 second, in the range of 0.1 seconds to 500 seconds, or 1 second to 30 seconds.

The fuel and oxidant used for the regeneration mode can be the same as those disclosed in U.S. Pat. No. 7,943,808. Optionally, the fuel is derived from, comprises, consists essentially of, or consists of one or more of hydrogen, CO, methane, methane containing streams, such as coal bed methane, biogas, associated gas, natural gas and mixtures or components thereof, etc. The fuel typically comprises one or more of molecular hydrogen, synthesis gas (mixtures of CO and $H_2$), and hydrocarbon, such as ≥10.0 wt. % hydrocarbon, or ≥50.0 wt. % hydrocarbon, or ≥90.0 wt. % hydrocarbon. The oxidant is typically one or more of molecular oxygen, ozone, and air, including molecular oxygen in air.

Once a fuel of the desired caloric content (heating value) has been selected, the amounts of fuel and oxidant conducted to the reactor during regeneration mode can be specified in terms of the amount of oxidant needed for combusting the accumulated coke deposits ("$OC_a$") and the amount of oxidant ("$OC_b$") needed for the substantially stoichiometric combustion of the fuel. Typically, the oxidant supplied during regeneration mode is Z. ($OC_a+OC_b$), wherein Z is in the range of 0.8 to 10.0, e.g., in the range of 1.0 to 3.0, and the amounts $OC_a$ and $OC_b$ are on a molar basis. When Z>1.0, the excess oxidant can be utilized, e.g., for one or more of (i) moderating the reaction temperature during regeneration mode (as disclosed in U.S. Pat. No. 7,943,808), (ii) conveying heat within the reactor from one zone to another, and (iii) replenishing an SOC located in the reaction zone. Typically, oxidant flow rate and fuel flow rate remain substantially constant for the duration regeneration mode.

Other streams can be provided to the reactor during regeneration mode, e.g., one or more diluent streams. When used, diluent can be provided with the oxidant and/or fuel. Suitable diluents (which can be a diluent mixture) include one or more of, e.g., non-oxidant oxygenate (water, carbon dioxide, etc.), non-combustible species, such as molecular nitrogen ($N_2$), and fuel impurities, such as hydrogen sulfide. For example, the oxidant can comprise 60.0 mole % to 95.0 mole % diluent and 5.0 mole % to 30.0 mole % molecular oxygen per mole of the oxidant, such as when the oxidant is air. Optionally, the oxidant has a mass ratio of diluent to molecular oxygen in the range of 0.5 to 20.0, e.g., in the range of 4.0 to 12.0.

Combustion conditions during regeneration mode (fuel combustion and coke deposit combustion) are selected to provide a temperature profile during regeneration having a maximum temperature in the vicinity of the dehydrocyclization catalyst that is ≤750° C. Exceeding this temperature during regeneration has been found to result in catalyst de-alumination and/or loss of structure, leading to an undesirable loss of catalyst acidity. Typically, combustion conditions including fuel choice and amount, oxidant choice and amount, the location of fuel combustion in the reactor, etc., are selected to provide a maximum temperature to which the dehydrocyclization catalyst is exposed during regeneration of about 700° C., more typically of about 650° C. Typically, excess oxidant (e.g., oxidant beyond that need for stoichiometric fuel combustion and catalyst coke combustion and any SOC replenishment) is not used. Lessening the amount of excess oxidant beneficially limits the size of the exotherm where coke is burned off the dehydrocyclization catalyst. In certain aspects, combustion conditions during regeneration mode are selected to achieve a temperature at the location where the oxidant first contacts the dehydrocyclization catalyst that is 350° C., e.g., 325° C., such as 300° C.

The invention is not limited to the forgoing aspects, for example, the following additional aspects are within the scope of the invention.

In other aspects, the invention relates to a catalytic reverse-flow reactor which comprises a reactor vessel, a dehydrocyclization catalyst, and conduits for a feed, a reaction product, a fuel, an oxidant, and a combustion product. The reactor vessel has an internal volume which includes a heat-transfer zone, a reaction zone opposed to the heat-transfer zone, and a third zone located between the heat-transfer and reaction zones. The dehydrocyclization catalyst is located in the reaction zone. The zones are in fluidic communication with one another. The feed conduit is in fluidic communication with the heat-transfer zone to convey a forward flow of a feed comprising non-aromatic hydrocarbon to the reaction zone. The reaction zone is adapted to both (i) catalytically react at least a portion of the feed with the dehydrocyclization catalyst to produce coke deposits and a reaction product comprising aromatic hydrocarbon and (ii) establish a forward flow of the reaction product through the third zone to the heat-transfer zone. The reaction product conduit is in fluidic communication with the heat-transfer zone to convey a forward flow of the reaction product away from the heat-transfer zone and out of the reverse-flow reactor. The fuel conduit is in fluidic communication with the heat-transfer zone to convey a reverse flow of a fuel through the heat-transfer zone toward the third zone. The oxidant conduit is in fluidic communication with the heat-transfer zone to convey a reverse flow of an oxidant to the third zone. The third zone is adapted to combust at least a portion of the fuel with a first portion of the oxidant and convey to the reaction zone at least (A) a reverse-flow of a first combustion product and (B) a reverse flow of un-combusted oxidant. The reaction zone is adapted to oxidize the coke deposits with the un-combusted oxidant flow to produce a second combustion product. The combustion product conduit is in fluidic communication with the reaction zone to convey a reverse-flow of the first and second combustion products away from the reaction zone and out of reverse-flow reactor. The catalytic reverse-flow reactor also includes at least one flow controller to establish during a first time interval the forward flows of the non-aromatic hydrocarbon feed and the reaction product for a time duration of, e.g., 90 seconds or less, and to establish during a second time interval the reverse flows of flow of the fuel, the oxidant, and the combustion product. Optionally, the reaction zone has a substantially non-monotonic temperature profile at the start of the first time interval.

Other aspects of the invention relate to the dehydrocyclization of a feed comprising $C_{2+}$ non-aromatic hydrocarbon. The reaction is carried out in a reverse-flow reactor which comprises a pre-cooled heat-transfer zone, a pre-heated reaction zone opposed to the heat-transfer zone, and a third zone located between the heat-transfer zone and the reaction zone. The heat-transfer zone, the reaction zone, and the third zone are all in fluidic communication with one another. A dehydrocyclization catalyst located in the reaction zone, the dehydrocyclization catalyst comprising a molecular sieve component and a dehydrogenation component. As in the preceding aspects, reaction mode is carried out during a first time interval and regeneration mode is carried out during a second time interval, but in these aspects the first time interval has a time duration of no more than 90 seconds. A forward flow of the feed is established to the reaction zone during reaction mode. Heat is transferred from the reaction zone to the feed, to produce a heated feed. The heated feed is reacted in the reaction zone in the presence of the dehydrocyclization catalyst under dehydrocyclization conditions which include a temperature ≥400° C. and a pressure ≥0 psi gauge (psig) (101 kPa). The reaction produces a forward flow of a reaction product comprising molecular hydrogen and aromatic hydrocarbon. The reaction also deposits coke on or proximate to the dehydrocyclization catalyst. The forward flow of reaction product is conducted from the reaction zone, through the third zone and the heat-transfer zone, and away from the reverse-flow reactor. Heat is transferred from the reaction product to the heat-transfer zone, which heats the heat-transfer zone and cools the reaction product. At the end of the first interval, feed flow to the reaction zone is decreased or halted. Regeneration mode is carried out during the second time interval. Regeneration mode utilizes an oxidant and a gaseous fuel. The fuel and oxidant have a characteristic molar ratio $M_c$, that if achieved would result in stoichiometric combustion of the fuel. At the start of regeneration mode, a reverse flow of the fuel and a reverse flow of the oxidant are established to the heat-transfer zone at an oxidant flow:fuel flow molar ratio > $M_c$. Heat is transferred from the heat-transfer zone to at least the oxidant flow in order to (i) heat the oxidant to a temperature at which it can combust with the fuel and (ii) re-cool the heat-transfer zone. A reverse-flow of combustion products is produced by combusting with the heated oxidant flow (A) at least a portion of the deposited coke and (B) at least a portion of the fuel flow, wherein ≥50 wt. % of the fuel flow combustion occurs in the third zone. The reaction zone is re-heated by transferring heat from the combustion products, which are conducted away from the reaction zone and out of the reverse-flow reactor. At the end of the second time interval, the reverse flow of fuel and the reverse flow of oxidant are decreased or halted.

All patents, test procedures, and other documents cited herein, including priority documents, are fully incorporated by reference to the extent such disclosure is not inconsistent. It is not intended that the scope of the claims appended hereto be limited to the descriptions set forth herein but rather that the claims be construed as encompassing all the features of patentable novelty which reside herein, including all features which would be treated as equivalents thereof by those skilled in the art to which this disclosure pertains. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of," "selected from the group of consisting of," or "is" preceding the recitation of the composition, component, or components, and vice versa.

The invention claimed is:

1. A hydrocarbon dehydrocyclization process, the process comprising:
    (a) providing a feed comprising $C_{2+}$ non-aromatic hydrocarbon;
    (b) providing an oxidant and a gaseous fuel;
    (c) providing a reverse-flow reactor, the reverse-flow reactor including
        (i) a pre-heated reaction zone, and
        (ii) a dehydrocyclization catalyst located in the reaction zone, the dehydrocyclization catalyst comprising a molecular sieve component and a dehydrogenation component;
    (d) during a first time interval,
        (i) establishing a forward flow of the feed to the reaction zone,
        (ii) transferring heat from the reaction zone to the feed to produce a heated feed and a cooled reaction zone,
        (iii) reacting at least a portion of the heated feed flow's $C_{2+}$ non-aromatic hydrocarbon in the presence of the dehydrocyclization catalyst under dehydrocyclization conditions which include a temperature of 400° C. to 700° C. and a pressure ≥0 psi gauge (psig) (101 kPa) to produce a forward flow of a reaction product comprising molecular hydrogen and aromatic hydrocarbon,
        (iv) depositing coke on or proximate to the dehydrocyclization catalyst,
        (v) conducting the forward flow of reaction product from the reaction zone and away from the reverse-flow reactor, and
        (vi) decreasing the feed flow to the reaction zone; and
    (e) during a second time interval,
        (i) establishing a reverse flow of the fuel and a reverse flow of the oxidant toward the reverse-flow reactor, the oxidant flow comprising first and second portions of the oxidant,
        (ii) combusting the first portion of the oxidant flow under combustion conditions with at least a portion of the fuel flow outside of the reaction zone to produce a reverse flow of a first combustion product toward the reaction zone,
        (iii) combusting within the reaction zone the second portion of the oxidant flow with at least a portion of the deposited coke to produce a reverse flow of a second combustion product in the reaction zone,
        (iv) conducting the reverse flows of the first and second combustion products away from the reaction zone and out of the reverse-flow reactor, wherein heat is transferred from the combustion products to the reaction zone to re-heat the reaction zone, and
        (v) decreasing the reverse flow of fuel and the reverse flow of oxidant,
    wherein the combustion of step (e)(ii) is carried out in the presence of a catalytically effective amount of at least one selective combustion catalyst, ≥95 wt. % of the fuel flow is combusted in the presence of the selective combustion catalyst, and the reaction zone has a non-monotonic temperature profile at the end of step (e).

2. The process of claim 1, wherein
    (i) the pressure is in the range of from 0 psig (101 kPa) to 300 psig (2170 kPa),
    (ii) the dehydrocyclization conditions further include a space velocity (GHSV) ≥1100 $hr^{-1}$, and
    (iii) the first time interval has a duration in the range of from 0.01 seconds to 30 seconds.

3. The process of claim 1, wherein the first time interval is in the range of from 0.1 seconds to 10 seconds.

4. The process of claim 3, wherein the first portion of the oxidant flow is ≥50wt. % of the oxidant flow.

5. The process of claim 1, wherein the feed comprises ≥75 wt. % of the $C_{2+}$ non-aromatic hydrocarbon, the $C_{2+}$ non-aromatic hydrocarbon comprising 10 wt. % to 40wt. % ethane, 20 wt. % to 50 wt. % propane, 20 wt. % to 50 wt. % butanes, and substantially saturated $C_{5+}$ hydrocarbon; and wherein the feed further comprises 1 wt. % or more of methane.

6. The process of claim 1, wherein
(i) the combustion conditions include combusting in the reaction zone ≥95 wt. % of the deposited coke and combusting ≥85 wt. % of the fuel flow outside of the reaction zone,
(ii) the temperature of the dehydrocyclization catalyst during step (e) is ≤650° C.,
(iii) the second time interval is in the range of from 0.1 second to 500 seconds, and
(iv) the process includes repeating steps (d) and (e).

7. The process of claim 1, wherein the dehydrocyclization catalyst includes
(i) at least 50 wt. % of the molecular sieve component, the molecular sieve component comprising one or more of MCM-22, ZSM-5, ZSM-11, ZSM-12, ZSM-22, ZSM-23, ZSM-35, and ZSM-48; and
(ii) at least 0.005 wt. % of the dehydrogenation component; the dehydrogenation components comprising one or more of Ga, Zn, Cu, Re, Mo, W, La, Fe, Ag, Pt, and Pd.

8. The process of claim 7, wherein
(i) the dehydrocyclization catalyst comprises at least 90 wt. % of the molecular sieve component and at least 1 wt. % of the dehydrogenation component;
(ii) the molecular sieve component comprises at least 90 wt. % of (A) ZSM-5and/or (B) ZSM-12;
(iii) the first dehydrogenation component comprises ≥90 wt. % of (A) Ga and/or (B) Zn;
(iv) the reaction achieves (A) a $C_{2+}$ hydrocarbon conversion of X wt. % and (B) a methane selectivity of Y wt. %; and
(v) when (A)X>60 then Y≤40,(B)X is in the range of 50 to 60 then Y≤20, and (C) X<50 then Y≤15.

9. The process of claim 1, wherein
(i) the reaction zone further comprises at least one pre-oxidized solid oxygen carrier (SOC);
(ii) step (d) further comprises increasing aromatic hydrocarbon yield by reducing the pre-oxidized SOC to release oxygen, and combusting at least a portion of the released oxygen with at least a portion of the reaction product's molecular hydrogen; and
(iii) step (e) further comprises re-oxidizing the SOC with a third portion of the oxidant flow.

10. A hydrocarbon conversion process, comprising:
(a) providing a feed comprising $C_{2+}$ non-aromatic hydrocarbon;
(b) providing an oxidant and a gaseous fuel, the fuel and oxidant having a characteristic molar ratio $M_c$ for stoichiometric combustion of the fuel;
(c) providing a reverse-flow reactor, the reverse-flow reactor including
(i) a pre-cooled heat-transfer zone,
(ii) a pre-heated reaction zone opposed to the heat-transfer zone,
(iii) a third zone located between the heat-transfer and reaction zones, the third zone being in fluidic communication with the heat-transfer and reaction zones,
(iv) a dehydrocyclization catalyst located in the reaction zone, the dehydrocyclization catalyst comprising a molecular sieve component and a dehydrogenation component, and
(v) at least one pre-oxidized solid oxygen carrier (SOC) in the reaction zone;
(d) during a first time interval having a time duration of no more than 90 seconds,
(i) establishing a forward flow of the feed to the reaction zone,
(ii) transferring heat from the reaction zone to the feed to produce a heated feed and a cooled reaction zone,
(iii) reacting the flow of heated feed in the presence of the dehydrocyclization catalyst under dehydrocyclization conditions which include an average temperature ≥400° C. and a pressure ≥0 psi gauge (psig) (101 kPa) to produce a forward flow of a reaction product comprising molecular hydrogen and aromatic hydrocarbon, a deviation in temperature across the dehydrocyclization catalyst in the reaction zone at a beginning of the first time interval being 10% or less of the average temperature in °C.,
(iv) increasing aromatic hydrocarbon yield by reducing the pre-oxidized SOC to release oxygen. and combusting at least a portion of the released oxygen with at least a portion of the reaction product's molecular hydrogen
(v) depositing coke on or proximate to the dehydrocyclization catalyst,
(vi) conducting the forward flow of reaction product from the reaction zone, through the third and heat-transfer zones, and away from the reverse-flow reactor, wherein heat is transferred from the reaction product to the heat-transfer zone to heat the heat-transfer zone, and
(vii) decreasing the teed flow to the reaction zone; and
(e) during a second time interval,
(i) establishing a reverse flow of the fuel and a reverse flow of the oxidant to the heat-transfer zone at an oxidant flow : fuel flow molar ratio >$M_c$, and transferring heat from the heat-transfer zone to at least the oxidant flow to re-cool the heat-transfer zone,
(ii) producing a reverse-flow of combustion products by combusting with the heated oxidant flow (A) at least a portion of the deposited coke and (B) at least a portion of the fuel flow, wherein ≥50 wt. % of the fuel flow combustion occurs in the heat-transfer zone and/or the third zone,
(iii) re-oxidizing the SOC with a third portion of the oxidant flow
(iv) conducting the reverse flow of combustion products away from the reaction zone and out of the reverse-flow reactor, wherein heat is transferred from the combustion products to the reaction zone to re-heat the reaction zone, and
(v) decreasing the reverse flow of fuel and the reverse flow of oxidant to the heat-transfer zone.

11. The process of claim 10, wherein
(i) the average temperature is in the range of from 400° C. to 700° C.,
(ii) the pressure is in the range of from 0 psig (101 kPa) to 300 psig (2170 kPa),
(iii) the dehydrocyclization conditions further include a space velocity (GHSV)≥1100 hr$^{-1}$, and
(iv) the first time interval has a duration in the range of from 0.01 seconds to 30seconds.

12. The process of claim 10, wherein the first time interval is in the range of from 0.1 seconds to 10 seconds.

13. The process of claim 10, wherein the coke combustion of step (e)(ii)(A) consumes an amount of the heated oxidant in the range of from 0.1 wt. % to 10 wt. %.

14. The process of claim 10, wherein the feed comprises ≥75 wt. % of the $C_{2+}$ non-aromatic hydrocarbon, the $C_{2+}$ non-aromatic hydrocarbon comprising 10 wt. % to 40 wt. % ethane, 20 wt. % to 50 wt. % propane, 20 wt. % to 50 wt. % butanes, and substantially saturated $C_{5+}$ hydrocarbon; and wherein the feed further comprises 1 wt. % or more of methane.

15. The process of claim 10, wherein
 (i) the combustion conditions include combusting in the reaction zone ≥95 wt. of the deposited coke and combusting in the third zone ≥85 wt. % of the fuel flow,
 (ii) the temperature of the dehydrocyclization catalyst during step (e) is ≤650° C.,
 (iii) the second time interval is in the range of from 0.1 second to 500 seconds,
 (iv) the oxidant flow: fuel flow molar ratio is in the range of from $1.1 \cdot M_c$ to $10 \cdot M_c$; and
 (v) the process includes repeating steps (d) and (e).

16. The process of claim 10, wherein the dehydrocyclization catalyst includes
 (i) at least 50 wt. % of the molecular sieve component, the molecular sieve component comprising one or more of MCM-22, ZSM-5, ZSM-11, ZSM-12, ZSM-22, ZSM-23, LSM-35, and ZSM-48; and
 (ii) at least 0.005 wt. % of the dehydrogenation component; the dehydrogenation components comprising one or more of Ga, Zn, Cu, Re, Mo, W, La, Fe, Ag, Pt, and Pd.

17. The process of claim 16, wherein
 (i) the dehydrocyclization catalyst comprises at least 90 wt. % of the molecular sieve component and at least 1 wt. % of the dehydrogenation component;
 (ii) the molecular sieve component comprises at least 90 wt. % of (A) ZSM-5 and/or (B) ZSM-12;
 (iii) the first dehydrogenation component comprises ≥90 wt. % of (A) Ga and/or (B) Zn; and
 (iv) the reaction achieves a $C_{2+}$ hydrocarbon conversion ≥65 wt %.

18. The process of claim 10, wherein
 (i) the fuel combustion of step (e)(ii)(B) consumes ≥75 wt. % of the heated oxidant,
 (ii) the third zone includes a catalytically effective amount of at least one selective combustion catalyst, and
 (iii) ≥95 wt. % of the fuel flow is combusted in the third zone.

* * * * *